(12) United States Patent
Bordy et al.

(10) Patent No.: US 11,555,774 B2
(45) Date of Patent: Jan. 17, 2023

(54) METHOD FOR ANALYSING MICROORGANISMS

(71) Applicant: COMMISSARIAT A L'ENERGIE ATOMIQUE ET AUX ENERGIES ALTERNATIVES, Paris (FR)

(72) Inventors: Thomas Bordy, Grenoble (FR); Olivier Cioni, Grenoble (FR); Camille Deforceville, Anglars (FR); Ondrej Mandula, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 459 days.

(21) Appl. No.: 16/614,971

(22) PCT Filed: May 18, 2018

(86) PCT No.: PCT/EP2018/063085
§ 371 (c)(1),
(2) Date: Nov. 19, 2019

(87) PCT Pub. No.: WO2018/215337
PCT Pub. Date: Nov. 29, 2018

(65) Prior Publication Data
US 2020/0200672 A1    Jun. 25, 2020

(30) Foreign Application Priority Data
May 22, 2017   (FR) ...................................... 1754535

(51) Int. Cl.
*G01N 15/14*  (2006.01)
*C12Q 1/06*   (2006.01)
(Continued)

(52) U.S. Cl.
CPC ........... *G01N 15/1434* (2013.01); *C12Q 1/06* (2013.01); *G01N 15/1475* (2013.01);
(Continued)

(58) Field of Classification Search
CPC ........... G01N 15/1434; G01N 15/1475; G01N 2015/1006; G01N 2015/1454; C12Q 1/06;
(Continued)

(56) References Cited

U.S. PATENT DOCUMENTS

| 6,979,828 | B2 * | 12/2005 | Tokuda | ................. C12M 41/36 250/461.2 |
| 9,644,229 | B2 * | 5/2017  | Brubacher | ............... C12Q 1/04 |

(Continued)

FOREIGN PATENT DOCUMENTS

| WO | WO 2016/097092 A1 | 6/2016 |
| WO | WO 2016/151248 A1 | 9/2016 |
| WO | WO 2016/151249 A1 | 9/2016 |

OTHER PUBLICATIONS

International Search Report dated Jul. 27, 2018 in PCT/EP2018/063085 filed on May 18, 2018.
(Continued)

*Primary Examiner* — Gregory M Desire
(74) *Attorney, Agent, or Firm* — Oblon, McClelland, Maier & Neustadt, L.L.P.

(57) ABSTRACT

A method for analyzing microorganisms arranged in a sample is provided, the sample including a viability marker to modify an optical property of the microorganisms in different ways depending on whether they are dead or alive, the method including illumination of the sample and acquisition of an image of the latter by an image sensor, the image sensor then being exposed to an exposure light wave; determining positions of different microorganisms from the acquired image; applying a propagation operator to calculate
(Continued)

at least one characteristic value of the exposure light wave at each radial position and at a plurality of distances from the detection plane representing a change in the characteristic value between the image sensor and the sample; and identifying living microorganisms according to each profile.

13 Claims, 5 Drawing Sheets

(51) Int. Cl.
*G02B 21/36* (2006.01)
*G03H 1/00* (2006.01)
*G03H 1/04* (2006.01)
*G01N 15/10* (2006.01)

(52) U.S. Cl.
CPC ......... *G02B 21/367* (2013.01); *G03H 1/0005* (2013.01); *G03H 1/0443* (2013.01); *G01N 2015/1006* (2013.01); *G01N 2015/1454* (2013.01); *G03H 2001/005* (2013.01); *G03H 2001/0447* (2013.01); *G03H 2226/02* (2013.01); *G03H 2226/11* (2013.01)

(58) Field of Classification Search
CPC .. G02B 21/367; G03H 1/0005; G03H 1/0443; G03H 2001/0447; G03H 2001/005; G03H 2226/02; G03H 2226/11
See application file for complete search history.

(56) References Cited

U.S. PATENT DOCUMENTS

| | | | |
|---|---|---|---|
| 10,845,286 B2* | 11/2020 | Allier | G01N 21/453 |
| 10,928,404 B2* | 2/2021 | Demirci | B01L 3/502715 |
| 2008/0090736 A1* | 4/2008 | Zhao | G16B 20/20 |
| | | | 506/8 |
| 2017/0102374 A1* | 4/2017 | Drabinsky | G01N 33/4833 |
| 2017/0284926 A1 | 10/2017 | Perraut et al. | |
| 2018/0080760 A1 | 3/2018 | Allier et al. | |
| 2018/0113064 A1 | 4/2018 | Allier et al. | |

OTHER PUBLICATIONS

Feizi, A. et al., "Rapid, portable and cost-effective yeast cell viability and concentration analysis using lensfree on-chip microscopy and machine learning," Lab on a Chip, The Royal Society of Chemistry, vol. 16, 2016, pp. 4350-4358, XP055446711.

* cited by examiner

METHOD FOR ANALYSING MICROORGANISMS

TECHNICAL FIELD

The technical field of the invention is the characterization of microorganisms, notably the characterization of yeasts or bacteria.

PRIOR ART

The use of microorganisms such as yeasts or bacteria, or derivatives thereof, finds many applications in many fields. In the food sector, for example, yeasts are used extensively in various sectors, such as baking, winemaking, brewing or the manufacture of milk products. The application of yeasts or bacteria relates to many foodstuffs, via probiotics, the latter being added for example to cereals or to animal feeds. Besides the food industry, many industrial fields may employ microorganisms. These are for example agriculture or horticulture, with the development of phytosanitary products or fertilizers that are more environmentally friendly, or the production of biofuels obtained from plants. Other applications relate to the field of pharmacy and medical diagnostics.

For quality control purposes, the step of characterization of these microorganisms constitutes an essential link in the production chain. Microbiological controls are frequently carried out on samples taken from culture media, in order to detect and count live microorganisms. Culture in Petri dishes is still widely used, but has certain drawbacks, in particular the preparation, the analysis time and the impossibility of detecting microorganisms that are alive but are nonculturable.

Techniques for direct counting have been developed, using for example viability markers able to alter the optical properties of microorganisms in different ways depending on whether they are dead or alive. Such markers may act on the color or a fluorescence property of the microorganisms being examined. However, the detection step, carried out using a microscope, is generally long, as the field of view is small.

The work by Feizi "Rapid, portable and cost effective yeast cell viability and concentration analysis using lensfree on-chip microscopy and machine learning", Lab Chip, 2016, 16, 4350-4358, describes a method for characterizing yeasts *Saccharomyces cerevisiae*, based on lensfree microscopy. The device presented is simple, and makes it possible to discriminate dead yeasts from live yeasts while offering a large field of view. Methylene blue is mixed beforehand with the culture medium in which the yeasts being examined are immersed. The method comprises acquisition of an image of the culture medium by an image sensor, and the application of a holographic propagation operator to the acquired image considering multiple propagation distances, so as to perform digital focusing, which makes it possible to establish a so-called optimal distance. Once the optimal distance has been obtained, each yeast is classified according to a live or dead category as a function of an indicator established on the basis of an image reconstructed at said optimal distance.

In other documents there have been attempts to characterize cells while avoiding having recourse to exogenous markers. For example, document WO2016/151249 describes a method for analyzing cells, disposed in a culture medium, without labeling. Addition of a marker is considered in this document as possibly affecting the development of the cells. Document WO2016/151248 describes a method for identifying particles, for example blood particles, while also avoiding prior labeling of the latter. Document WO2016/097092 describes an imaging technique according to a defocused configuration, for identifying a microorganism from defocused images relative to a focusing plane of an optical system.

The inventors have proposed an alternative to the method described in Feizi's work cited above, for performing a classification between dead and live microorganisms via a method that is simple and inexpensive in computation time. Moreover, as described in the description, the method provides fuller analysis of the live microorganisms.

PRESENTATION OF THE INVENTION

The invention relates firstly to a method for analyzing microorganisms, the microorganisms being disposed in a sample, the sample comprising a viability marker able to modify an optical property of the microorganisms in different ways depending on whether they are dead or alive, the method comprising the following steps:
  a) illuminating the sample using a light source, the light source emitting an incident light wave that is propagated toward the sample along a propagation axis;
  b) using an image sensor, acquiring an image of the sample, formed in a detection plane, the sample being arranged between the light source and the image sensor, each image being representative of a so-called exposure light wave, to which the image sensor is exposed under the effect of the illumination;
the method being characterized in that it also comprises the following steps:
  c) determining radial positions of different microorganisms in a plane parallel to the detection plane, each radial position being associated with a microorganism;
  d) based on the image acquired in step b), applying a propagation operator, to calculate at least one characteristic quantity of the exposure light wave, at each radial position determined in step c), and at a plurality of distances from the detection plane;
  e) forming a profile, representing the variation of the characteristic quantity calculated in step d) along an axis parallel to the propagation axis and passing through each radial position determined in step c), each profile being associated with a microorganism;
  f) as a function of each profile formed in step e), identifying the live microorganisms.

"Characteristic quantity" means for example a module or a phase of the exposure light wave, or a combination thereof.

"Applying a propagation operator based on an image" means that the propagation operator is applied to said image or to an image resulting from a transformation of said image, for example a square root of said image, as well as optional normalization of the image.

Step f) may comprise identification of the dead microorganisms.

According to one embodiment, the method comprises, following step f), a step g) of analyzing the microorganism's ability to divide, step g) comprising the following substeps for at least one microorganism considered to be alive in step f):
  gi) obtaining a first observed image of the sample, at a first instant, the observed image comprising regions of interest associated respectively with microorganisms, and detecting a region of interest associated with said microorganism;

gii) acquiring an image of the sample at a second instant, subsequent to the first instant, and obtaining a second observed image of the sample starting from the image acquired at the second instant;

giii) detecting, on the second observed image, a region of interest corresponding to the microorganism;

giv) comparing the regions of interest detected in substeps gi) and giii);

gv) determining the microorganism's ability to divide as a function of the comparison carried out in substep giv).

Step g) then makes it possible to identify, among the microorganisms identified as being alive, the microorganisms that are viable but nonculturable. It can be applied to each microorganism considered to be alive following step f).

In substeps gi) and gii), the first observed image and the second observed image can be obtained by applying a propagation operator respectively on the basis of an image acquired at the first instant and on the basis of an image acquired at the second instant. The first observed image may result from the image acquired in step b).

The time interval between the first instant and the second instant may be between 5 hours and 70 hours.

According to one embodiment, in step d) the propagation operator is applied on the basis of the image acquired in step b), according to a plurality of propagation distances, so as to obtain a stack of complex images.

According to another embodiment, step d) comprises the following substeps:

di) applying a propagation operator, based on the image acquired in step b), in order to calculate a complex image, called a reference image, representative of the sample, in a reference plane;

dii) applying a propagation operator to the reference image, so as to obtain complex images, called secondary complex images, at different distances from the reference plane along the propagation axis, the secondary complex images and the reference image forming a stack of complex images;

diii) determining a radial position of microorganisms from the images of the stack of complex images obtained in substep dii).

According to this embodiment, the first observed image may be derived from the reference image, being for example the image of the module or the image of the phase of the reference image.

Step c) may be carried out starting from a complex image of the stack of complex images resulting from step d), or starting from the reference complex image, considering the module or the phase of said complex image.

According to one embodiment, the viability marker induces coloration of the microorganisms when they are dead, according to a coloration spectral band. In step a), the sample is illuminated according to an illumination spectral band, the illumination spectral band not comprising all or part of the coloration spectral band.

The method may comprise one of the following features, taken individually or according to the combinations that are technically achievable:

In step d), the characteristic quantity is determined from the module or the phase of the exposure light wave, at each distance from the detection plane.

Step f) comprises classifying each profile according to a first class, corresponding to profiles characteristic of live microorganisms, and a second class, corresponding to profiles characteristic of dead microorganisms. The classification of each profile may be carried out as a function of its form or of a maximum value or a minimum value of the profile.

No image-forming optical system is arranged between the sample and the image sensor.

An image-forming optical system is arranged between the sample and the image sensor, the optical system having an object focal plane, the sample extending in a plane of the sample, the plane of the sample being offset relative to the object focal plane.

The invention further relates to a device for analyzing microorganisms disposed in a sample, the device comprising:

a light source able to emit an incident light wave that is propagated toward the sample;

an image sensor;

a support, configured for holding the sample between the light source and the image sensor;

a processor, configured for receiving an image of the sample acquired by the image sensor and for carrying out steps c) to f) of a method according to the first aim of the invention.

According to one embodiment, no magnifying or image-forming optical system extends between the image sensor and the sample, when the latter is held on the support.

According to another embodiment, an image-forming optical system is arranged between the sample and the image sensor, the optical system having an object focal plane, the sample extending in a plane of the sample, the device being arranged in such a way that the plane of the sample is offset relative to the object focal plane.

Other advantages and features will become clearer from the following description of particular embodiments of the invention, given as nonlimiting examples, and represented in the figures listed hereunder.

FIGURES

Figure 3A:
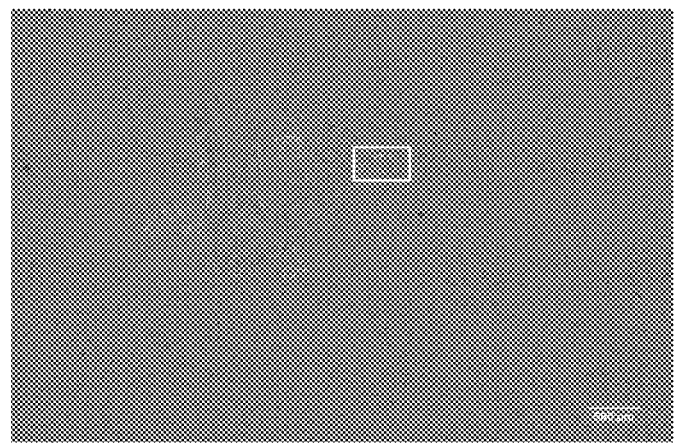
Figure 3B:
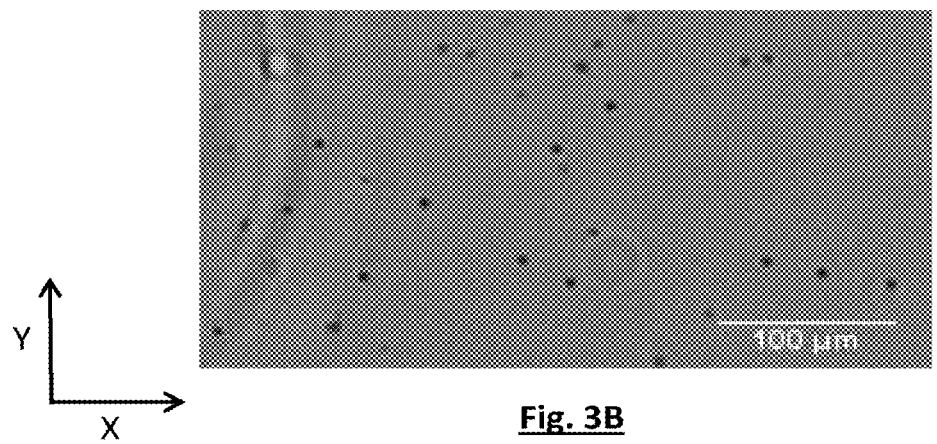
Figure 3C:
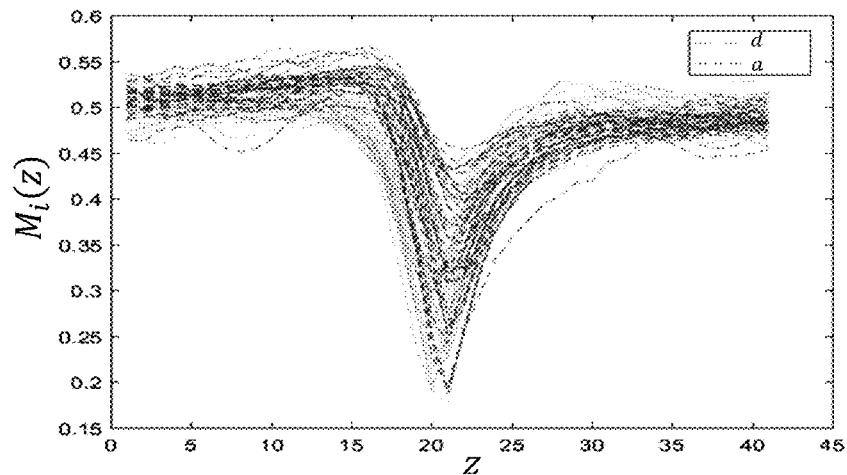
Figure 3D:
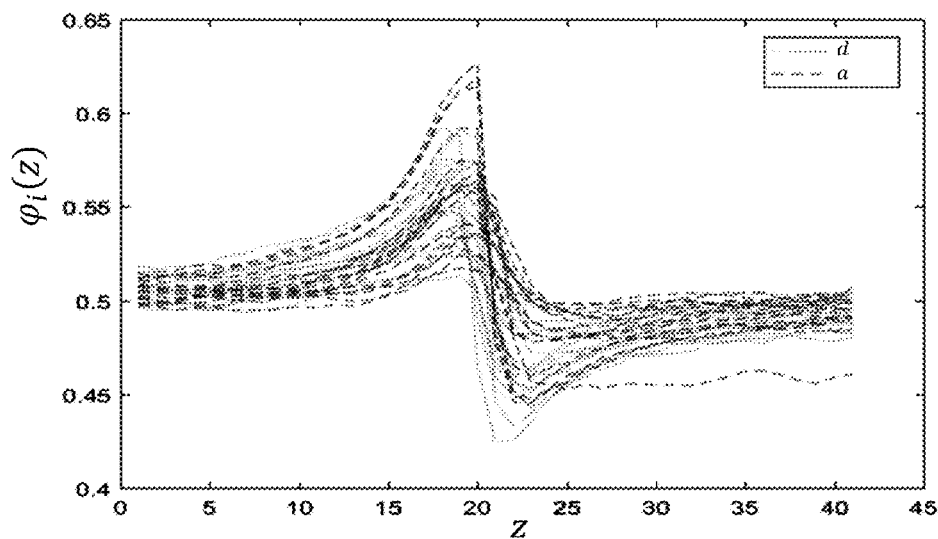

FIG. 3A is an image of the module of a reconstructed complex image from an image of a sample acquired at a first instant. This image was obtained during an experimental assay carried out using a sample comprising yeasts. FIG. 3B is a detail from FIG. 3A. FIGS. 3C and 3D respectively show amplitude and phase profiles of a light wave reconstructed from the image in FIG. 3B, each profile passing through a radial position, in the plane of the image sensor, with which a yeast is associated.

Figure 4A:
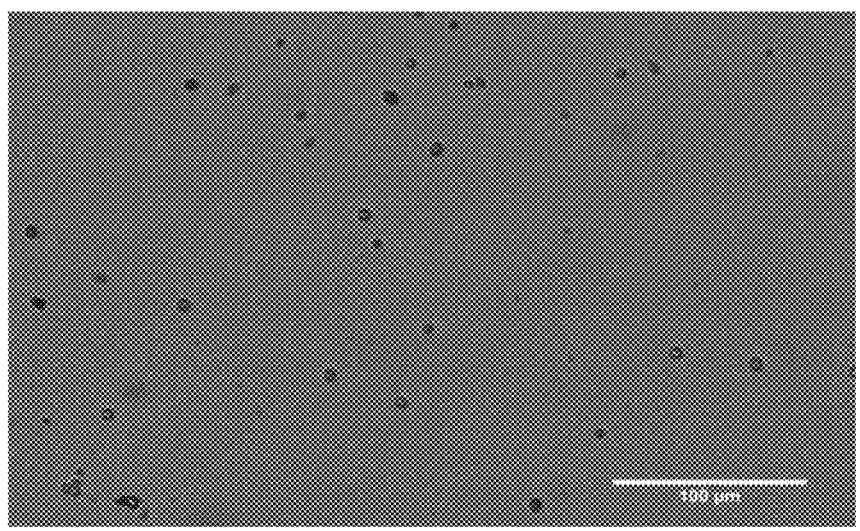
Figure 4B:
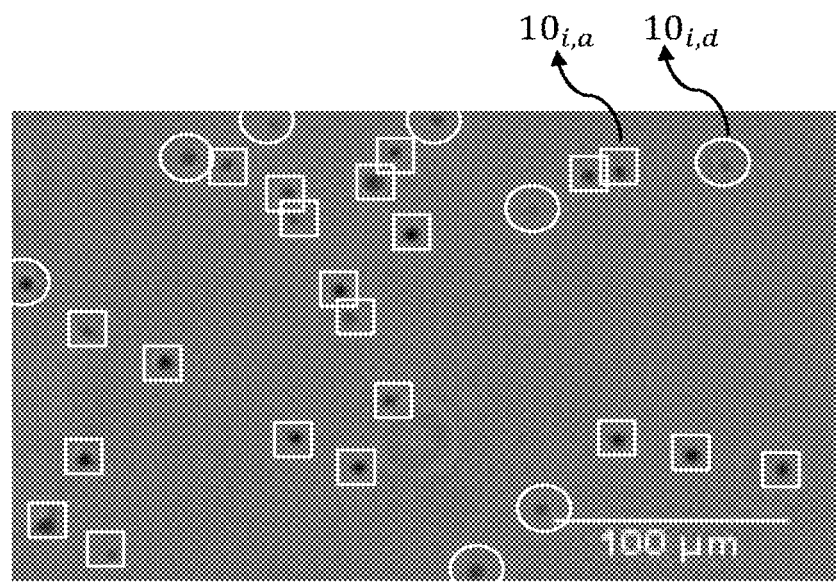
Figure 4C:
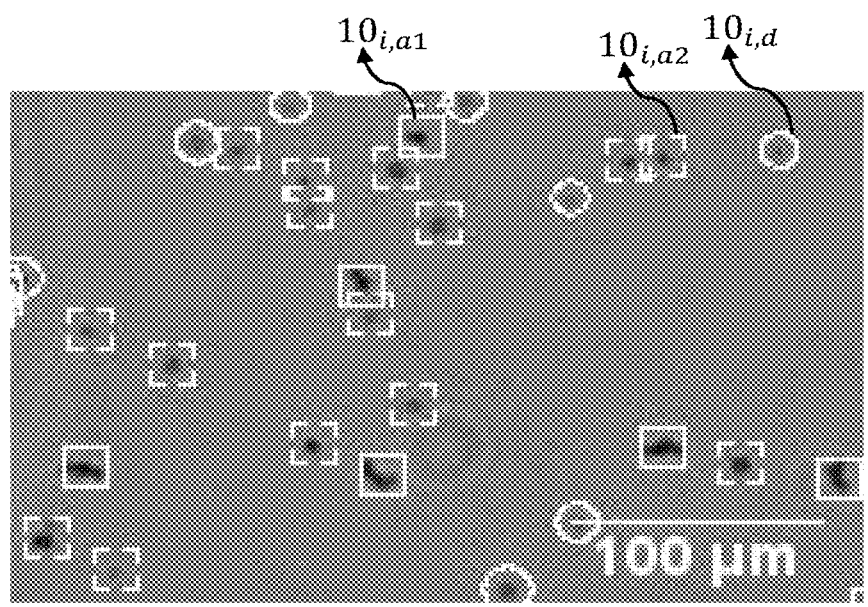

FIG. 4A shows a microscope observation of yeasts. FIG. 4B shows, on a part of the image shown in FIG. 3B, the yeasts considered to be dead and those considered to be alive, by applying the invention. This image corresponds to the state of the yeasts at a first instant. FIG. 4C shows an image obtained by holographic reconstruction starting from an image acquired at a second instant. It shows the state of the yeasts at the second instant. Comparison between FIGS. 4B and 4C makes it possible to identify, among the live yeasts, yeasts that are viable but nonculturable.

DESCRIPTION OF PARTICULAR EMBODIMENTS

Figure 1:
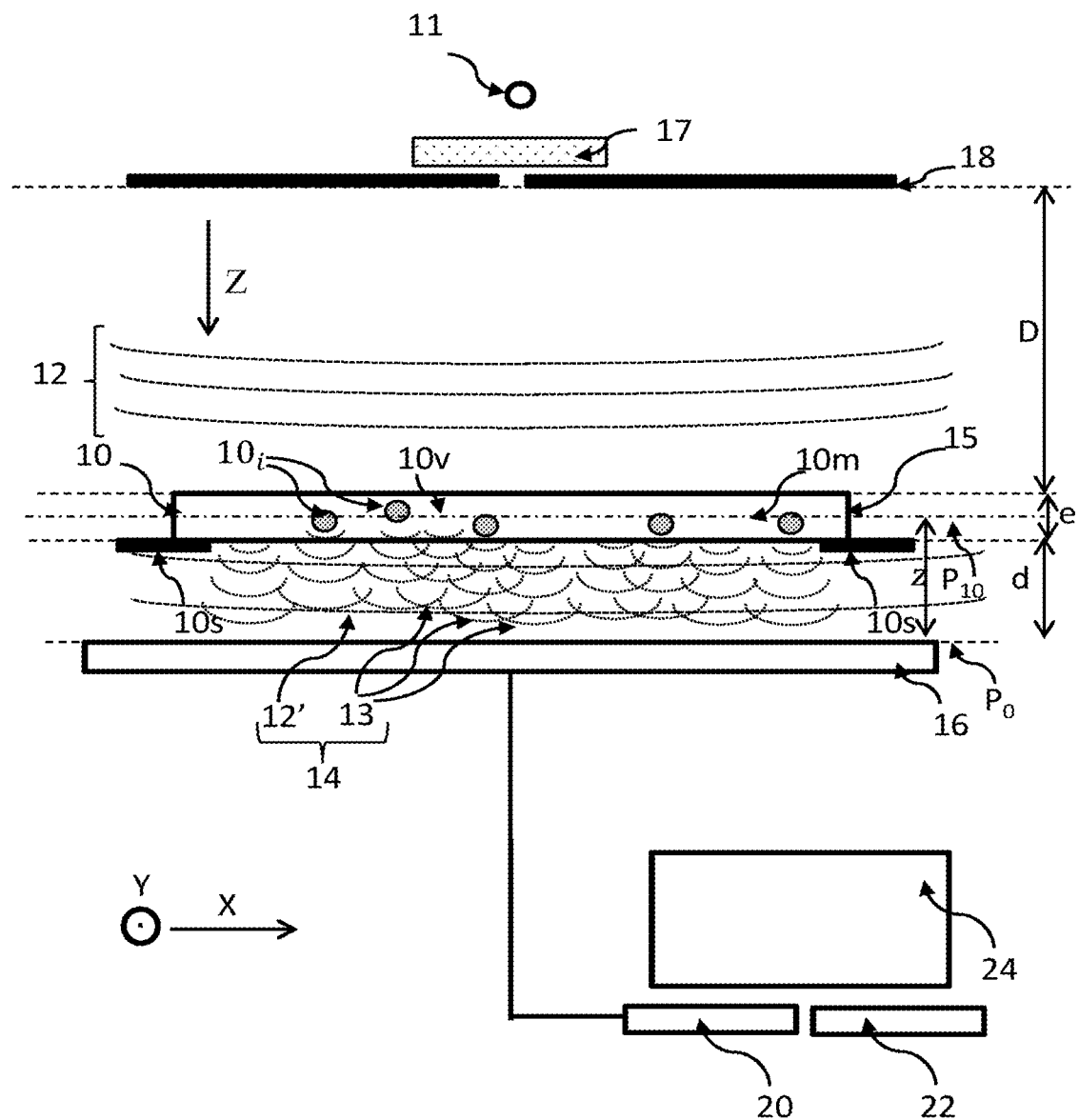
FIG. 1 shows an example of a device according to the invention.

FIG. 1 shows an example of a device according to the invention. A light source 11 is able to emit a light wave 12, called the incident light wave, which is propagated toward a sample 10, along a propagation axis Z. The light wave is emitted according to an illumination spectral band $\Delta\lambda$.

Sample 10 is a sample that we wish to characterize. It notably comprises a medium $10m$ in which microorganisms $10_i$ are immersed. The medium $10m$ is generally a culture medium, comprising nutrients allowing microorganisms to develop. "Microorganism" means notably a yeast, a bacterium, a spore, a fungus or a cell, whether it is a eukaryotic cell or a prokaryotic cell, or a microalga.

The sample also comprises a viability marker $10_v$, the latter being able to modify an optical property of a microorganism $10_i$ in different ways depending on whether the microorganism is alive or dead. As mentioned in connection with the prior art, modification of the visual appearance means for example modification of the color of the microorganism. The use of these viability markers is well known. They may be methylene blue, or Trypan Blue. The modification of the optical property may also be a modification of the intensity of fluorescence light emitted by a microorganism being analyzed, using for example a viability indicator, sometimes denoted by the term fluorogenic marker, examples of such markers being described in WO9855861A1, or in the publication Kwolek-Mirek M "Comparison of methods used for assessing the viability and vitality of yeast cells", FEMS Yeast Res 14 (2014) 1068-1079.

In the example described below, the viability indicator $10_v$ is methylene blue. Under its action, the dead microorganisms are colored according to a coloration spectral band $\Delta\lambda'$, in this case blue, whereas the live microorganisms remain translucent.

In this example, sample 10 is contained in a fluidic chamber 15. The fluidic chamber 15 is for example a fluidic chamber of the Gene Frame® type with a thickness e=250 µm. The thickness e of the sample 10, along the propagation axis, typically varies between 10 µm and 1 cm, and is preferably between 20 µm and 500 µm. The sample extends in a plane $P_{10}$, called the plane of the sample, perpendicular to the propagation axis Z. It is held on a support 10 s at a distance d from an image sensor 16. The concentration of microorganisms may vary between 500 per microliter and 5000 per microliter.

The distance D between the light source 11 and the fluidic chamber 15 is preferably greater than 1 cm. It is preferably between 2 and 30 cm. Advantageously, the light source seen by the sample is considered to be a point source. This signifies that its diameter (or its diagonal) is preferably less than a tenth, better still less than a hundredth of the distance between the fluidic chamber 15 and the light source. In FIG. 1, the light source is a light-emitting diode. It is generally associated with a diaphragm 18, or spatial filter. The aperture of the diaphragm is typically between 5 µm and 1 mm, preferably between 50 µm and 500 µm. In this example, the diaphragm is supplied by Thorlabs under the reference P150S and its diameter is 150 µm. The diaphragm may be replaced with an optical fiber, a first end of which is placed facing the light source 11 and its second end is placed opposite the sample 10. The device shown in FIG. 1 also comprises a diffuser 17, arranged between the light source 11 and the diaphragm 18. The use of a diffuser of this kind eliminates constraints on centering the light source 11 relative to the aperture of the diaphragm 18. The function of said diffuser is to distribute the light beam produced by an elementary light source 11 over a cone of angle $\alpha$. Preferably, the diffusion angle $\alpha$ varies between 10° and 80°.

Alternatively, the light source may be a laser source, such as a laser diode. In this case it is not useful to combine it with a spatial filter or a diffuser.

Preferably, the emission spectral band $\Delta\lambda$ of the incident light wave 12 has a width under 100 nm. "Spectral band width" means the full width at half maximum of said spectral band.

According to one embodiment, the light source 11 comprises several elementary light sources $11_k$, each being able to emit an incident light wave $12_k$ in a spectral band $\alpha\lambda_k$. Preferably, the spectral bands $\alpha\lambda_k$ of the different light sources $11_k$ are different from one another.

The sample 10 is arranged between the light source 11 and the aforementioned image sensor 16. The latter preferably extends parallel, or approximately parallel, to the plane $P_{10}$ over which the sample extends. The term "approximately parallel" signifies that the two elements need not be rigorously parallel, an angular tolerance of some degrees, less than 20° or 10°, being permitted. In this example, the sample extends in a plane XY, perpendicular to the propagation axis Z.

The image sensor 16 is able to form an image $I_0$ of the sample 10 in a detection plane $P_0$. In the example shown, it is an image sensor comprising a pixel matrix, of the CCD type or a CMOS. The detection plane $P_0$ preferably extends perpendicularly to the propagation axis Z of the incident light wave 12. The distance d between the sample 10 and the pixel matrix of the image sensor 16 is preferably between 50 µm and 2 cm, preferably between 100 µm and 2 mm.

Note, in this embodiment, the absence of a magnifying or image-forming optical system between the image sensor 16 and the sample 10. This does not preclude the optional presence of focusing microlenses at the level of each pixel of the image sensor 16, the latter not having the function of magnifying the image acquired by the image sensor, but for optimizing the efficacy of detection.

Under the effect of the incident light wave 12, the microorganisms $10_i$ present in the sample can generate a diffracted wave 13, capable of producing interference at the level of the detection plane $P_0$, in particular with a part of the incident light wave 12' transmitted by the sample. Moreover, the sample can absorb a part of the incident light wave 12. Thus, the light wave 14 transmitted by the sample, and to which the image sensor 16 is exposed, denoted by the term "exposure wave", may comprise:
- a component 13 resulting from the diffraction of the incident light wave 12 by each microorganism of the sample;
- a component 12' resulting from the transmission of the incident light wave 12 by the sample, where a part of the latter may be absorbed in the sample.

These components form interferences in the detection plane. Thus, the image acquired by the image sensor comprises interference patterns (or diffraction patterns), and each interference pattern may be associated with a microorganism $10_i$ of the sample.

A processor 20, for example a microprocessor, is able to process each image $I_0$ acquired by the image sensor 16. In particular, the processor is a microprocessor connected to a programmable memory 22 in which a sequence of instructions is stored for performing the operations of image processing and calculation described in this description. The processor may be coupled to a screen 24 for displaying images acquired by the image sensor 16 or calculated by the processor 20.

An image $I_0$ acquired by the image sensor 16, also called a hologram, is not able to give a sufficiently accurate representation of the sample observed. As described in connection with the prior art, a holographic propagation operator h may be applied to each image acquired by the image sensor, in order to calculate a quantity representative of the exposure light wave 14. It is then possible to reconstruct a complex expression A of the light wave 14 at any point of coordinates (x, y, z) in space, and in particular in a reconstruction plane $P_z$ located at a distance $|z|$ from the image sensor 16, called the reconstruction distance, this reconstruction plane preferably being the plane in which the sample $P_{10}$ extends, with:

$A(x, y, z)=I_0(x, y, z)*h$ * denoting the convolution product operator, or, and preferably, $A(x, y, z)=\sqrt{I_0(x,y,z)}*h$, or else:

$$A(x, y, z) = \frac{\sqrt{I_0(x, y, z)}}{\overline{I_0}} * h, \overline{I_0}$$

being a mean value of the acquired image.

The function or the propagation operator h is to describe the propagation of light between the image sensor 16 and a point with coordinates (x, y, z), located at a distance $|z|$ from the image sensor. It is then possible to determine the module M(x, y, z) and/or the phase $\varphi(x, y, z)$ of the light wave 14, at this distance $|z|$, called the reconstruction distance, with:

$M(x,y,z)=\text{abs}[A(x,y,z)]$;

$\varphi(x,y,z)=\arg[A(x,y,z)]$;

The operators abs and arg denote the module and the argument, respectively.

The propagation operator is for example the Fresnel-Helmholtz function, such that:

$$h(x, y, z) = \frac{1}{j\lambda z} e^{j2\pi \frac{z}{\lambda}} \exp\left(j\pi \frac{x^2 + y^2}{\lambda z}\right).$$

In other words, the complex expression A of the light wave 14, at any point with coordinates (x, y, z) in space, is such that: $(x, y, z)=M(x, y, z)e^{j\varphi(x,y,z)}$.

Hereinafter in this description, the coordinates (x,y) denote a radial position in a radial plane XY perpendicular to the propagation axis Z. The coordinate z denotes a coordinate along the propagation axis Z.

The complex expression A is a complex quantity whose argument and module are respectively representative of the phase and the intensity of the exposure light wave 14 detected by the image sensor 16. The product of convolution of the image $I_0$ by the propagation operator h makes it possible to obtain a complex image $A_z$ representing a spatial distribution of the complex expression A in a reconstruction plane $P_z$, extending at a distance $|z|$ from the detection plane $P_0$. In this example, the detection plane $P_0$ has the equation z=0. The complex image $A_z$ corresponds to a complex image of the sample in the reconstruction plane $P_z$. It also represents a two-dimensional spatial distribution of the optical properties of the exposure wave 14. A method of this kind, denoted by the term holographic reconstruction, notably makes it possible to reconstruct an image of the module or phase of the exposure light wave 14 in the reconstruction plane.

It is possible to form images $M_z$ and $\varphi_z$ respectively representing the module or the phase of a complex image $A_z$ in a plane $P_z$ located at a distance $|z|$ from the detection plane $P_0$, with $M_z=\text{mod}(A_z)$ and $\varphi_z=\arg(A_z)$.

The inventors have developed a method for characterizing microorganisms, for example yeasts, said method being described in connection with FIG. 2, some results of which are illustrated in FIGS. 3A to 3D and 4A to 4C. These results were obtained according to the following experimental conditions:

Sample 10: it comprises active dry yeasts ADY dispersed in a Sabouraud culture medium, to which a solution of methylene blue (0.1 mg·ml$^{-1}$) has been added. The concentration is about 1500 yeasts per µl.

Light source 11: Cree MC-E Color light-emitting diode, comprising three light-emitting diodes that can be activated simultaneously or successively, each diode respectively emitting in the following spectral bands $\Delta\lambda$: 450-465 nm; 520-535 nm; 620-630 nm. Only the spectral band 620-630 nm was employed in the tests presented hereunder.

Image sensor 16: Sensor, 8 bits CMOS monochrome 3884×2764 pixels, each pixel with a side measuring 1.67 µm, the detection area extending over about 30 mm$^2$. Taking into account the thickness of the fluidic chamber, the sample volume addressed by each image amounts to 7.5 µl.

Distance D between the light source 11 and the sample 10: 5 cm.

Distanced between the sample 10 and the image sensor 16: 1000 µm.

Thickness e of the fluidic chamber 15: 250 µm.

Diameter of the aperture of the spatial filter 18: 150 µm.

The main steps of the method of counting according to the invention are:

Acquisition, by the image sensor, of an image $I_0$ of the sample in one or more illumination spectral bands, the image being acquired at a first instant $t_1$.

Starting from the acquired image, obtaining a first observed image $I(t_1)$, corresponding to the first instant, then, starting from this observed image, detecting regions of interest $ROI_i$ corresponding to the microorganisms $10_i$ and determining their respective radial coordinates $(x_i, y_i)$, the term "radial" signifying in a plane parallel to the detection plane.

Starting from the acquired image, calculating a characteristic quantity, for example the module or the phase, of the exposure light wave 14, at different distances from the sample, called reconstruction distances; this notably involves obtaining a stack of complex images representing the exposure light wave, the complex images extending in parallel planes arranged between the detection plane $P_0$ and the plane of the sample $P_{10}$.

Forming a profile representing the variation of the characteristic quantity as a function of the reconstruction distance, each profile being associated with a microorganism.

Starting from one or more profiles associated with each microorganism, identifying live or dead microorganisms.

The method may comprise acquiring an image of the sample at a second instant $t_2$, the second instant being subsequent to the first instant $t_1$, and obtaining a second observed image $I(t_2)$ associated with the second instant. By comparing the observed images respectively associated with the first and the second instant it is possible to identify, among the microorganisms considered to be alive, the microorganisms that are viable but nonculturable.

The concept of a microorganism that is viable but non-culturable (VBNC) is familiar to a person skilled in the art. It is a live microorganism, as it displays metabolic activity, but it is unable to divide in the medium in which it is immersed. Therefore it cannot grow in its medium. The VBNC state may be influenced by various factors, for example the temperature, the content of certain nutrients or chemical elements in the environment or the culture medium, exposure to light, factors that may induce stress in the microorganism. Identification of VBNC microorganisms allows rigorous characterization of the quality of the sample in question.

Step 100: Acquisition of an image $I_0$ of the sample 10 by the image sensor 16, said image forming a hologram. One of the advantages of the lensfree configuration shown in FIG. 1 is the wide observed field, allowing a large sample volume to be addressed simultaneously. This makes it possible to observe several microorganisms simultaneously, and thus obtain a rapid characterization of the sample. The observed field depends on the size of the image sensor, being slightly less than the detection area of the latter, owing to the spacing between the pixels of the sensor and the sample. The observed field is generally greater than 10 mm$^2$, and is typically between 10 mm$^2$ and 50 mm$^2$, which is significantly greater than with a microscope. In this example, this image is acquired at a first instant $t_1$ and can be designated $I_0(t_1)$.

Step 110: Formation of a reference image. Owing to the absence of an image-forming optical system, the acquired image $I_0$ may comprise a large number of interference patterns, and may not be easily exploitable for locating the microorganisms present in the observed field. The latter are more easily identifiable starting from a reconstructed complex image by applying a holographic propagation operator to the acquired image. In this example, this complex image is a reference image $A_{ref}$, obtained by performing a holographic reconstruction in a reference plane $P_{ref}$ on an image obtained from the acquired image $I_0$.

A first solution is to apply the propagation operator to the acquired image $I_0$, or preferably to the square root of the acquired image $\sqrt{I_0}$, optionally normalized by the mean value $\overline{I_0}$ of the acquired image. The reference image $A_{ref}$ is a complex image comprising phase and amplitude information of the light wave 14 to which the image sensor 16 is exposed. The reference plane is a plane advantageously perpendicular to the propagation axis Z, and/or parallel to the detection plane $P_0$. It is preferably the plane of the sample $P_{10}$. In fact, it is generally in this plane that the spatial resolution of a reconstructed complex image is best, said principle forming the basis of so-called digital focusing algorithms.

However, the acquired image does not comprise information relating to the phase of the exposure wave 14. Therefore holographic reconstruction is performed on the basis of incomplete optical information, based solely on the intensity of the light wave collected on the image sensor. Improvement of the quality of holographic reconstruction is the subject of many developments, using algorithms often called "Phase retrieval", allowing determination of the phase of the light wave to which the image sensor is exposed. This type of algorithm makes it possible to limit the reconstruction noise that affects the reconstructed complex image $A_{ref}$. An example of an algorithm that can be used is described for example in US2012/0218379.

According to one possibility, the sample is illuminated successively or simultaneously in different spectral bands $\Delta\lambda_k$, and an image $I_0(\Delta\lambda_k)$ representative of each spectral band is acquired in the detection plane $P_0$. The algorithm makes it possible to obtain a complex image $A_{ref}(\Delta\lambda_k)$ of the sample 10, in the reference plane, in each spectral band $\Delta\lambda_k$. The complex images thus obtained may be combined, for example by averaging their module and their phase in each pixel, making it possible to form the reference image $A_{ref}$. Alternatively, the reference complex image is a complex image $A_{ref}(\Delta\lambda_k)$ in a spectral band $\Delta\lambda_k$. An algorithm of this kind was described in the publication S.N.A. Morel, A. Delon, P. Blandin, T. Bordy, O. Cioni, L. Hervé, C. Fromentin, J. Dinten, and C. Allier, "Wide-Field Lensfree Imaging of Tissue Slides," in *Advanced Microscopy Techniques IV*; and *Neurophotonics II*, E. Beaurepaire, P. So, F. Pavone, and E. Hillman, eds., Vol. 9536 of SPIE Proceedings (Optical Society of America, 2015) as well as in the patent application FR1554811 filed on May 28, 2015, and more precisely in the iterative steps 100 to 500 described in that application. It was shown that the use of two or three different spectral bands makes it possible to obtain a good quality of reconstruction.

Another possibility, which corresponds to the preferred embodiment, is to reconstruct a reference complex image on the basis of a sample image acquired when the sample is illuminated in a single spectral band $\Delta\lambda$. The reference complex image may be obtained using an iterative algorithm as described in patent application FR1652500 filed on Mar. 23, 2016, and more precisely according to steps 110 to 160 described in said patent application.

The coordinate $z_{ref}$ of the reference plane $P_{ref}$ is determined either a priori, notably when the position of the sample is controlled relative to the image sensor 16, or by means of digital focusing. Digital focusing makes it possible to define a focusing plane $P_{focus}$ reconstructing several images and defining a clarity criterion of each reconstructed image. The focusing plane $P_{focus}$ corresponds to that in which the reconstructed image has an optimal clarity criterion. It corresponds to the plane in which a majority of the microorganisms extend. The reference image $A_{ref}$ is then formed in a reference plane $P_{ref}$ corresponding to the focusing plane $P_{focus}$. The focusing plane corresponds to a plane over which the sample extends.

The complex image $A_{ref}$ is designated as being a reference image, as it serves as a basis for forming profiles, on the basis of which the microorganisms in the sample are characterized. FIG. 3A shows an image of the module $M_{ref}$ of the reference complex image obtained using the algorithm described in the preceding paragraph.

Step 120: construction of a stack of images.

This step comprises applying a propagation operator h to the reference complex image $A_{ref}$ in order to calculate complex images $A_{ref,z}$, called secondary, along the propagation axis Z. During this step, the reference complex image $A_{ref}$ is propagated according to a plurality of reconstruction distances z, using a propagation operator h as defined above, so as to have a plurality of complex images, called secondary, $A_{ref,z}$ reconstructed at the different distances z from the reference plane $P_{ref}$. Thus, this step comprises determining a plurality of complex images $A_{ref,z}$ such that:

$$A_{ref,z} = A_{ref} * h_z \text{ with } z_{min} \leq z \leq z_{max}.$$

In this way we obtain a stack of complex images $A_{ref,z_{min}} \ldots A_{ref,z_{max}}$.

The values $z_{min}$ and $z_{max}$ are the minimum and maximum coordinates, along the Z axis, between which the reference complex image is propagated. Preferably, the complex images are reconstructed according to a plurality of coordinates z between the sample 10 and the image sensor 16. The inventors considered that it was preferable to obtain secondary complex images on either side of the reference plane $P_{ref}$, in such a way that $z_{min} \leq z_{ref} \leq z_{max}$. In contrast to the image $I_0$ acquired by the image sensor 16, the reference complex image correctly describes the exposure light wave 14, in particular at the level of its phase. Consequently, it is considered that the secondary images $A_{ref,z}$, obtained by propagation of the reference image, form a good descriptor of the propagation of the exposure light wave 14 along the propagation axis Z. Thus, the secondary complex images are calculated quickly, without requiring the use of an iterative method such as that used for calculating the reference complex image $A_{ref}$. The method consisting of applying an iterative algorithm for establishing a reference complex image $A_{ref}$(step 110) and then obtaining secondary complex images by applying a propagation operator h to the reference complex image makes it possible to obtain a stack of complex images $A_{ref,z}$, optimizing the calculating means.

Preferably, two adjacent reconstruction planes are spaced apart according to a fine mesh, comprised for example between 5 μm and 50 μm, and for example 25 μm. It is a local propagation, as it is performed on a distance between 500 μm and 2 μm on either side of the reference plane $P_{ref}$, for example at ±500 μm. Based on a reconstruction over a distance of 500 μm on either side of the reference plane $P_{ref}$, and a distance between two adjacent planes of 20 μm, the reference complex image $A_{ref}$ is propagated over forty reconstruction planes $P_{ref,z}$, so as to form that many secondary complex images, $A_{ref,z}$.

Figure 2:
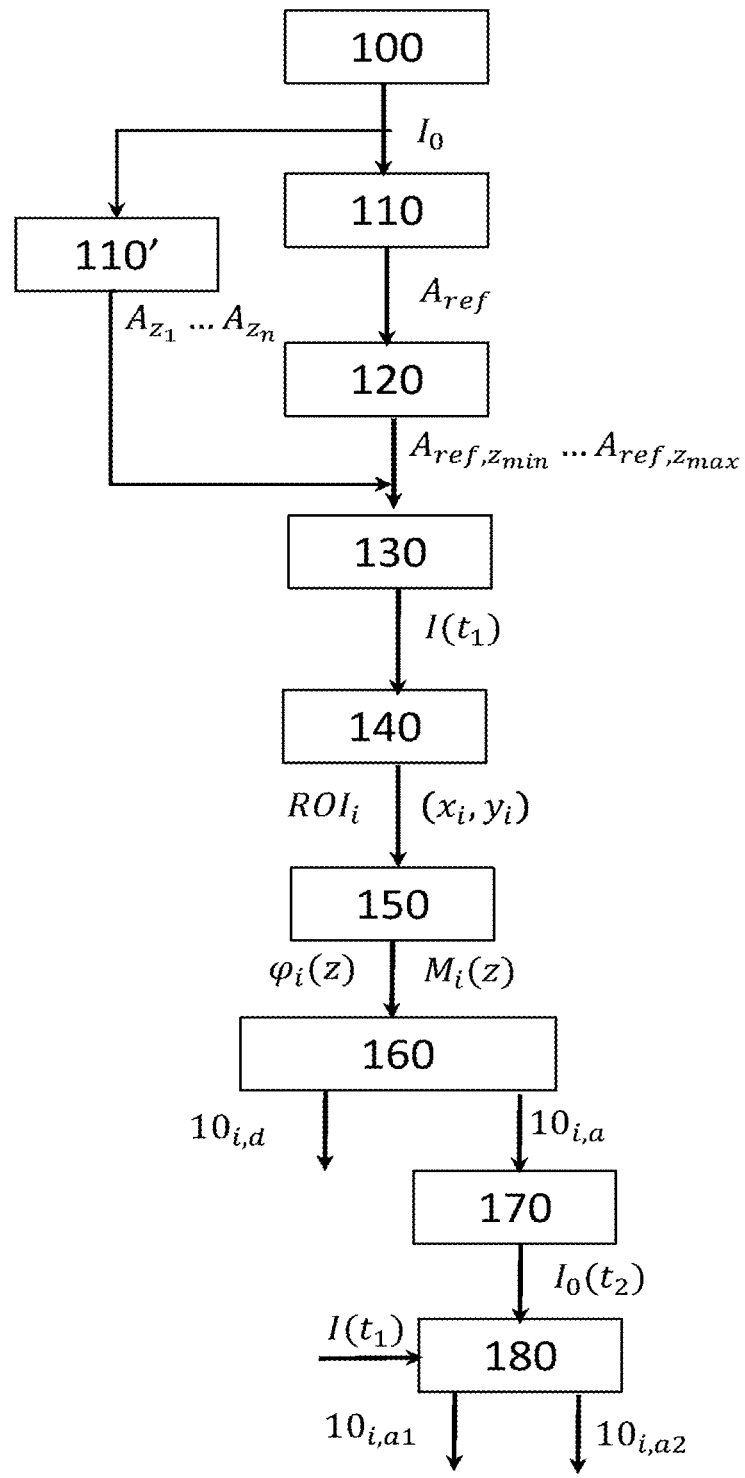
FIG. 2 illustrates the main steps of a method for identifying live microorganisms as well as, among the latter, microorganisms that are viable but nonculturable.

Alternatively, steps 110 and 120 may be replaced with a propagation starting from the image $I_0$ acquired in step 100, according to step 110' shown in FIG. 2. The propagation may be performed for example by applying a propagation operator to the square root $\sqrt{I_0}$ of this image, optionally normalized by the mean value $\overline{I_0}$, on different propagation distances $z_1 \ldots z_n$. It may be a simple application of a propagation operator h, in which case the reconstructed images $A_{z_1} \ldots A_{z_n}$, forming the stack of complex images, may be affected by considerable reconstruction noise. It may also be application of an iterative holographic reconstruction algorithm, for example one of the algorithms mentioned above, on different propagation distances $z_1 \ldots z_n$. This makes it possible to obtain reconstructed complex images of good quality, but the method is more expensive in terms of calculation. That is why it is preferable to employ an iterative reconstruction algorithm for forming the reference complex image, according to step 110, and to propagate the reference complex image by a simple application of a propagation operator, according to step 120. This makes it possible to obtain a good compromise between the quality of the images forming the stack of complex images and the computation time.

Step 130: detection of microorganisms in the sample.

This step aims to detect each microorganism present in the sample. It is performed starting from an observed image $I(t_1)$, called the first observed image, formed from an image $I_0(t_1)$ acquired by the image sensor at a first acquisition instant $t_1$, or starting from a complex image formed from the latter. Preferably, although this is not necessary, the image $I_0(t_1)$ corresponds to the image $I_0$ acquired in step 100 and the first observed image $I(t_1)$ results from this acquired image $I_0$, or from a complex image of the stack of images formed in step 120. It is preferable for the observed image $I(t_1)$ to be established on the basis of the module and/or phase of a reconstructed complex image in a plane over which the sample extends. It may be for example the reference complex image $A_{ref}$ obtained in step 110 or a secondary complex image $A_{ref,z}$ resulting from step 120. The first observed image $I(t_1)$ may be the image of the module $M_{ref}$ of the reference complex image $A_{ref}$, or the image $M_{ref,z}$ of the module of another complex image of the stack of images formed in step 120. It may also be the image $\varphi_{ref}$ of the phase of the reference complex image $A_{ref}$, or the image $\varphi_{ref,z}$ of the phase of another complex image of the stack of images formed in step 120. Generally the observed image is obtained from the module and/or phase of a complex image resulting from a propagation of an image $I_0$ acquired by the image sensor 16.

The detection of each microorganism is performed either manually by an operator, or automatically, by a morphologic analysis of the first observed image $I(t_1)$, taking into account that each microorganism $10_i$ may be associated, in the observed image, with a region of interest $ROI_i$ of predetermined shape, which can be detected easily. It may for example be a circular or ellipsoidal shape, or some other. For this, the method can detect each region of interest $ROI_i$ automatically, taking into account one or more morphologic criteria corresponding to a microorganism $10_i$, for example its area and its eccentricity. At least one microorganism $10_i$ corresponds to each region of interest $ROI_i$ detected. Algorithms based on a spatial correlation with predetermined shapes of regions of interest may also be used. As the volume of the sample 10 in the observation field of the image sensor 16 is known, this step makes it possible to determine a quantity $N_i$ or a concentration of microorganisms $10_i$ in the sample.

FIG. 3A corresponds to an image of the module $M_{ref}$ of a reference complex image of a sample described below, in connection with the examples. FIG. 3B corresponds to a detail of FIG. 3A.

Step 140: detection of the radial coordinates $(x_i, y_i)$ of each microorganism.

The microorganisms $10_i$ being detected, via the regions of interest $ROI_i$ that are respectively associated with them on the first observed image $I(t_1)$, their position $(x_i, y_i)$ in the radial plane XY, i.e. in a plane parallel to the detection plane, can be determined easily, for example by considering the centroid of the region of interest $ROI_i$ corresponding to each of them.

Step 150: forming a profile associated with each microorganism.

Based on each complex image forming the stack of images, a characteristic quantity of the exposure light wave 14 is determined at each radial position $(x_i, y_i)$ selected in step 140, and at a plurality of distances z of reconstruction of the reference plane $P_{ref}$, or of the detection plane $P_0$, then a profile is formed representing the variation of the characteristic quantity as a function of z, along the propagation axis Z. The characteristic quantity may notably be established based on the module and phase of the complex expression A describing the exposure light wave 14, using the images of the stack of complex images resulting previously from steps 120 or 110'.

FIGS. 3C and 3D show respectively a profile $M_i(z)$ of the module and a profile $\varphi_i(z)$ of the phase, passing through the radial positions $(x_i, y_i)$ selected on the image 3B. Each profile is obtained from the images of the stack of complex images established previously, by interpolating between the coordinates of two adjacent reconstructed images. Each profile is associated with a microorganism $10_i$.

Step 160: classification of each microorganism on the basis of the profiles formed in step 150.

Tests have shown that when a viability marker is introduced into the sample beforehand, the profiles $M_i(z)$ describing the variation of the module of the exposure light wave 14 may allow classification between the dead microorganisms $10_{i,d}$ or the live microorganisms $10_{i,a}$. These profiles are shown in FIG. 3C. In this figure, the coordinate z=20 corresponds to the focusing plane, i.e. the plane over which the microorganisms extend. One classification criterion is for example the maximum value taken by each profile $M_i(z)$ between the detection plane and the focusing plane. In FIG. 3C, it is the maximum value on a part of each profile $M_i(z)$ extending between the coordinates z=0 and z=20. When the maximum value of a profile is below a predetermined threshold, the microorganism is classified as being dead. Otherwise the microorganism is classified as being alive. In FIGS. 3C and 3D, the profiles corresponding to the microorganisms considered to be dead and alive are shown respectively with dotted lines (legend "d") and with dashes (legend "a").

The method preferably comprises steps 170 and 180 with the aim of identifying, among the microorganisms considered alive at the end of step 160, the microorganisms that are viable but nonculturable (VBNC) mentioned above.

Step 170: acquisition of a delayed image $I_0(t_2)$.

During step 130, a first observed image $I(t_1)$ was formed, representing the sample at a first instant, this first instant being designated $t_1$. Step 170 comprises acquisition, at a second acquisition instant $t_2$, subsequent to the first acquisition instant $t_1$, of a second image $I_0(t_2)$, called a delayed image, of sample 10 by means of the image sensor 16. The inventors observed that it was preferable for the time interval $\Delta t$ between the first instant $t_1$ and the second instant $t_2$ to be greater than 4 h, and preferably greater than 15 h or 20 h. For example, the time interval $\Delta t$ is between 4 and 72 hours, this interval being adjusted as a function of the time required for one division of the microorganism in question.

Step 180: formation of a delayed observed image and classification of the live microorganisms.

A second observed image $I(t_2)$ is formed on the basis of the image acquired at the second acquisition time. The second observed image $I(t_2)$ is preferably formed in the same way as the first observed image $I(t_1)$, so that the microorganisms are comparable on these two images. The microorganisms $10_{i,a}$ considered to be alive following step 160 are observed from the second observed image. Among these microorganisms, we identify the microorganisms whose morphology has changed relative to that observed on the first observed image $I(t_1)$. The change in morphology, obtained by comparing the first and the second observed image, must reflect at least one division of the microorganism during the time interval $\Delta t$. It can be determined manually or automatically, for example based on a comparison, between the two observed images $I(t_1)$ and $I(t_2)$, of the area or of a shape parameter of the region of interest $ROI_i$ associated, on each of these images, with each live microorganism. For example, when the area of a region of interest $ROI_i$ has increased by more than 20% between the two images, it is considered that the microorganism $10_{i,a}$ has divided or that a division is in progress. In this case, it is considered to be alive and able to divide, and therefore culturable. Otherwise it is considered to be viable but nonculturable.

FIGS. 4B and 4C show respectively:
the first observed image $I(t_1)$, described in connection with step 110, which corresponds to the module $M_{ref}$ of the reference complex image $A_{ref}$;
a second observed image $I(t_2)$, obtained from an image $I_0(t_2)$ acquired at a second instant $t_2$ 10 hours later than the first instant $t_1$. The second observed image is the module of a complex image obtained from the image $I_0(t_2)$ in the same way as the reference complex image $A_{ref}$.

In FIG. 4B, a white square is drawn round the microorganisms $10_{i,a}$ considered to be alive, whereas a white circle is drawn round the microorganisms $10_{i,d}$ considered to be dead. At the radial position $(x_i, y_i)$ corresponding to a microorganism $10_{i,a}$ considered to be alive, a comparison is made between the region of interest $ROI_i$ extending around the radial position at the first and second instants. On the basis of this comparison, the microorganisms $10_{i,a1}$ considered to be alive and culturable are surrounded by a square drawn with solid lines in FIG. 4C whereas the microorganisms $10_{i,a2}$ considered to be viable but nonculturable are surrounded by a square drawn with dotted lines.

The invention thus allows three categories of microorganisms to be counted: dead, alive and culturable, viable but nonculturable.

The inventors found that the performance of the method is enhanced when the illumination spectral band $\Delta\lambda$ is different from the coloration spectral band $\Delta\lambda'$ induced by the viability marker. Thus, when the viability marker is methylene blue, the illumination spectral band is preferably located in the red or in the infrared. Thus, it is preferable if the illumination spectral band and the coloration spectral band do not intersect, or intersect marginally. To intersect marginally means that the intersection between the two spectral bands is less than 10% or 20% of one of the two spectral bands.

The method described above was compared with a visual characterization of the microorganisms, the latter being observed with a microscope by an operator. FIG. 4A shows a view in the microscope at the second instant $t_2$. Visual characterization was used as the reference method, for qualifying the method according to the invention.

The following table shows the percentages of microorganisms considered to be dead, alive and culturable, or viable but nonculturable, obtained respectively by the method described above (1st line) and with the microscope (2nd line).

|  | dead | alive and culturable | viable but nonculturable |
| --- | --- | --- | --- |
| algorithm | 15 | 34 | 51 |
| reference | 12 | 24 | 64 |

The high proportion of yeasts that are viable but nonculturable is explained by the high temperature to which the sample was heated, generating stress promoting the viable but nonculturable state.

The reliability of the method is therefore comparable to conventional visual characterization carried out with the microscope. However, owing to the lensfree imaging configuration, the observed field is far larger than the observed field resulting from the use of a microscope. The invention for example allowed simultaneous characterization of 11574 yeasts distributed in the field of observation. The performance of the invention is therefore superior to the visual method in terms of quantity of microorganisms characterized in unit time. Moreover, the algorithm can be automated, and the reliability is demonstrated by the values given in the above table.

According to one variant, an image-forming optical system is arranged between the sample and the image sensor, the image sensor being positioned according to a so-called defocused configuration, the object focal plane of the optical system being offset from the plane over which the sample extends by a so-called defocusing distance. The defocusing distance may be between 5 µm and 5 mm, and preferably between 10 µm and 2 mm. In the same way as in the lensfree configuration, this configuration makes it possible to obtain an image in which each microorganism appears in the form of a diffraction pattern, interferences being produced between the light wave emitted by the light source and propagating as far as the image sensor and a diffraction wave generated by each microorganism. The method described in connection with steps 100 to 180 is applicable to images acquired according to such a configuration. However, a lensfree imaging configuration is preferred, for the larger field of observation that it provides.

Although described in relation to the characterization of yeasts, for purposes of quality control, the invention applies to other organisms such as those listed above, when we wish to obtain rapid and reliable analysis in a large field of observation.

The invention claimed is:

1. A method for analyzing microorganisms, the microorganisms being disposed in a sample, the sample comprising a viability marker configured to modify an optical property of the microorganisms in different ways depending on whether the microorganisms are dead or alive, the method comprising:
   a) illuminating the sample using a light source, the light source emitting an incident light wave that is propagated toward the sample along a propagation axis;
   b) using an image sensor, acquiring an image of the sample, formed in a detection plane, the sample being arranged between the light source and the image sensor, the image being representative of an exposure light wave, to which the image sensor is exposed under the effect of the illumination, the image comprising interference patterns between a part of the incident light wave transmitted by the sample and the diffraction of the incident wave by the microorganisms;
   c) determining radial positions of various microorganisms in a plane parallel to the detection plane, each radial position being associated with a microorganism;
   d) starting from the image acquired in b), applying a propagation operator, in order to calculate at least one characteristic quantity of the exposure light wave, at each radial position determined in c), and at a plurality of distances from the detection plane;
   e) forming a profile, representing the variation of the characteristic quantity calculated in d) along an axis parallel to the propagation axis and passing through each radial position determined in c), each profile being associated with a microorganism;
   f) identifying the live microorganisms, making use of each profile formed in e); and
   g) following f), analyzing the live microorganism's ability to divide,
   wherein g) further comprises, for at least one microorganism identified as live in f):
      $g_i$) obtaining a first observed image of the sample, at a first instant, the first observed image comprising regions of interest respectively associated with microorganisms and detecting a region of interest associated with said at least one microorganism,
      $g_{ii}$) acquiring an image of the sample at a second instant, the second instant being subsequent to the first instant, and obtaining a second observed image of the sample starting from the image of the sample acquired at the second instant,
      $g_{iii}$) detecting, on the second observed image, a region of interest corresponding to the at least one microorganism,
      $g_{iv}$) comparing the regions of interest detected in $g_i$) and $g_{ii}$), and
      $g_v$) determining the microorganism's ability to divide as a function of the comparison carried out in $g_{iv}$).

2. The method according to claim 1, wherein $g_v$) comprises identifying, among the live microorganisms, microorganisms that are viable but nonculturable.

3. The method according to claim 1, wherein in $g_i$) and $g_{ii}$), the first observed image and the second observed image are obtained by applying a propagation operator respectively starting from an image acquired at the first instant and starting from the image acquired at the second instant, respectively.

4. The method according to claim 1, wherein in $g_i$), the first observed image is obtained from the image acquired in b).

5. The method according to claim 1, wherein a time interval between the first instant and the second instant is between 5 hours and 70 hours.

6. The method according to claim 1, wherein in d) the propagation operator is applied starting from the image acquired in b), according to a plurality of propagation distances, so as to obtain a stack of complex images.

7. The method according to claim 1, wherein d) comprises:
   $d_1$) applying a propagation operator, starting from the image acquired in b) in order to calculate a complex image called the reference image, representative of the sample, in a reference plane;
   $d_{ii}$) applying a propagation operator to the reference image so as to obtain secondary complex images at different distances from the reference plane along the propagation axis, the secondary complex images and the reference image forming a stack of complex images; and
   $d_{iii}$) determining a radial position of microorganisms from the images of the stack of complex images obtained in $d_{ii}$).

8. The method according to claim 1, wherein:
   the viability marker induces a coloration of the microorganisms when the microorganisms are dead, according to a coloration spectral band, and
   in a), the sample is illuminated according to an illumination spectral band, the illumination spectral band not comprising all or part of the coloration spectral band.

9. The method according to claim 1, wherein, in d), the characteristic quantity is determined from a module or a phase of the exposure light wave, at each distance from the detection plane.

10. The method according to claim 1, wherein f) comprises classifying each profile according to:
    a first class, corresponding to profiles of live microorganisms, and
    a second class, corresponding to profiles of dead microorganisms.

11. The method according to claim 1, wherein the classification of each profile is carried out as a function of at least one of:
- the form of the profile,
- a maximum value of the profile, and
- a minimum value of the profile.

12. The method according to claim 1, wherein no image-forming optical system is arranged between the sample and the image sensor.

13. The method according to claim 1, wherein an image-forming optical system is arranged between the sample and the image sensor, the optical system having an object focal plane, the sample extending in a plane of the sample, the plane of the sample being offset relative to the object focal plane.

* * * * *